United States Patent [19]

Carcia et al.

[11] Patent Number: 4,753,916

[45] Date of Patent: Jun. 28, 1988

[54] METAL OXIDES OF MOLYBDENUM OR MOLYBDENUM AND TUNGSTEN

[75] Inventors: Peter F. Carcia; Eugene M. McCarron, both of Wilmington, Del.

[73] Assignee: E. I. Du Pont de Nemours and Company, Wilmington, Del.

[21] Appl. No.: 908,420

[22] Filed: Sep. 17, 1986

[51] Int. Cl.$^4$ .......................... B01J 23/28; B01J 23/30
[52] U.S. Cl. .................... 502/321; 423/593; 423/606
[58] Field of Search ................. 502/321; 423/593, 606

[56] References Cited

U.S. PATENT DOCUMENTS

| | | | |
|---|---|---|---|
| 1,998,626 | 4/1935 | Koenig | 502/321 X |
| 3,883,607 | 5/1975 | Neikam | 502/321 X |

OTHER PUBLICATIONS

McCarron, J. Chem. Soc., Chem. Commun., p. 336 (1986).
Kihlborg, Arkiv Kemi, 21:357 (1963).
Gunter, Journal of Solid State Chemistry, 5:354 (1972).
Boschen et al., Acta Cryst., B30:1795 (1974).
Oswald et al., Journal of Solid State Chemistry, 13:330 (1975).
Salje et al., Journal of Solid State Chemistry, 25:230 (1978).
Olenkova, React. Kinet. Catal. Lett., 22:339 (1983).
Hibble et al., Mat. Res. Bull., 20:343 (1985).
Ganapathi et al., J. Chem. Soc., Chem. Comm., 62 (1986).
Harb et al., C. R. Acad. Sc. Paris, t. 303, Serie II, No. 5, 1986, 349–352.
Harb et al. C. R. Acad. Sc. Paris, t. 303, Serie II, No. 6, 1986, 445–447.
Harb et al., C. R. Acad. Sc. Paris, t. 303, Serie II, No. 9, 1986, 789–792.

Primary Examiner—W. J. Shine

[57] ABSTRACT

A novel phase of molybdenum trioxide and mixed metal oxides of molybdenum and tungsten is disclosed.

18 Claims, 5 Drawing Sheets

F I G. 1
α-MoO₃
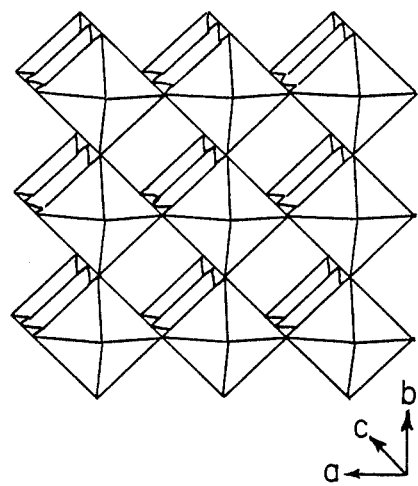
β-MoO₃
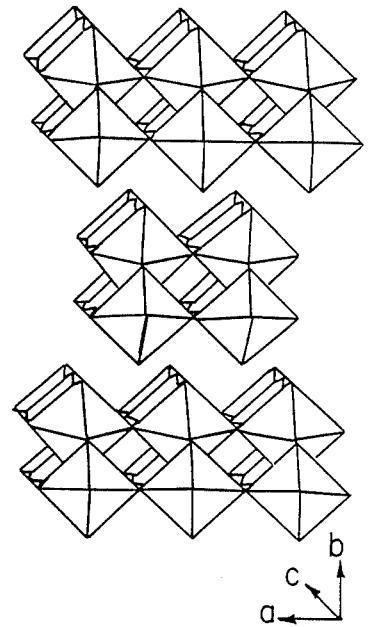

10 μM

10 μM

METAL OXIDES OF MOLYBDENUM OR MOLYBDENUM AND TUNGSTEN

BACKGROUND OF THE INVENTION

1. Field of the Invention

The present invention relates to a novel phase of molybdenum trioxide and mixed metal oxides of molybdenum and tungsten.

2. Background of the Invention

Molybdenum trioxide is known to crystallize with a two dimensional structure, which has been described as a layered structure, $MoO_{1/1}O_{2/2}O_{3/3}$, or as a chain structure, $Mo_{2/1}O_{2/2}$. Tungsten trioxide is known to adopt a $ReO_3$-related structure, $WO_{6/2}$. The dissimilar structure of $MoO_3$ is believed to be caused by the formation of oxomolybdenum cations which stabilize the layered structure. Novel phases of molybdenum trioxide and mixed metal-oxides of molybdenum and tungsten and methods for their preparation are of interest to the chemical industry.

Kihlborg, *Arkiv Kemi*, 21:357 (1963) discloses least square refinements of the crystal structure of molybdenum trioxide. The reference discloses that although it is usually regarded as an octahedral layer structure, the marked tendency towards four-fold coordination observed makes a description in terms of a tetrahedral chain structure equally appropriate. Gunter, *Journal of Solid State Chemistry*, 5:354 (1972) discloses topotactic dehydration of molybdenum trioxide hydrates. The reference discloses that the guiding elements of the two topotactic reactions are planes of corner-sharing octahedra. The conservation of these planes throughout the reactions was confirmed by scanning electron micrographs and X-ray diffraction.

Boschen et al., *Acta Cryst.*, B30:1795 (1974) discloses the crystal structure of the white isomer of $MoO_3(H_2O)$ The crystal is said to contain isolated double chains of $[MoO_3(H_2O)]$ octahedra with shared edges, three of the five oxygen atoms in each octahedron being shared by two other octahedra. Oswald et al., *Journal of Solid State Chemistry*, 13:330 (1975) discloses topotactic decomposition and crystal structure of white molybdenum trioxide-monohydrate. The structure is said to be built up from isolated double chains of strongly distorted $[MoO_5(H_2O)]$-octahedra sharing two common edges.

Salje et al., *Journal of Solid State Chemistry*, 25:239 (1978) discloses structural phase transition in mixed crystals of $W_xMo_{1-x}O_3$. The reference discloses that the structures of the system $WO_3$-$MoO_3$ are closely related to the corresponding $WO_3$ phases except for x less than 0.05% where an $MoO_3$-like structure was found. The structures of the system, except nearly pure $MoO_3$, are said to reveal perovskite-like arrangements of corner-sharing octahedral networks. Olenkova, *React. Kinet. Catal. Lett.*, 22:339 (1983) discloses structural peculiarities of orthorhombic $MoO_3$ prepared at low temperatures. The reference discloses that upon drying a solution prepared via the ion exchange of sodium molybdate on KU-2-8 cationite, $MoO_3$ is formed with water molecules in the interlayer space.

Hibble et al., *Mat. Res. Bull.*, 20:343 (1985) discloses hydrogen insertion compounds $H_xMo_yW_{1-y}O_3$ ($0 < x < 1.13$, $0.1 < y < 0.9$) of the mixed molybdenum tungsten oxides $Mo_yW_{1-y}O_3$. The reference discloses that two phases of the compounds are formed, a tetragonal phase $0.1 < x < 0.2$ and a cubic phase $x > 0.35$. Ganapathi et al., *J. Chem. Soc., Chem, Comm.*, 62 (1986) discloses a study of $MoO_3$, $WO_3$, and their solid solutions prepared by topotactic dehydration of the monohydrates. The reference discloses that dehydration of $Mo_{1-x}W_xO_3 \cdot H_2O$ ($0 < x < 1.0$) gives rise to oxides of '$ReO_3$' structure, the '$ReO_3$' structure transforming to the layered structure in the case of $MoO_3$. Reduced $Mo_{1-x}W_xO_3$ samples are said to exhibit disordered shear planes.

SUMMARY OF THE INVENTION

The present invention provides methods for preparing a composition of matter comprising $\beta$-$Mo_{1-x}W_xO_3$, wherein $0 \leq x < 1.0$. One method of the invention comprises spray-drying a solution of molybdic acid or molybdic and tungstic acids in appropriate concentrations and heating the resulting powder at a temperature of from about 275° C. to about 450° C. Another method of the invention comprises sputtering a molybdenum or mixed metal oxide target in appropriate concentrations onto a thermally floating substrate in an atmosphere comprising oxygen and an inert gas, wherein the oxygen is in an amount from about 5 to about 50 volume percent.

The present invention also provides a composition of matter comprising $\beta$-$Mo_{1-x}W_xO_3$, wherein $0 \leq x < 0.05$. This phase of the specified metal or mixed-metal oxide has a distorted three dimensional $ReO_3$ structure based on corner-linked octahedra. The structure is further characterized by the Raman spectrum shown in FIG. 3 and by the powder x-ray data of Table 1. The invention further provides a method for selective oxidation of methanol to formaldehyde comprising contacting methanol and oxygen in the presence of a catalytically effective amount of a composition of matter comprising $\beta$-$Mo_{1-x}W_xO_3$, wherein $0 \leq x < 1.0$, as catalysts.

BRIEF DESCRIPTION OF THE FIGURES

FIG. 1 shows a stylized representation of the structures of $\beta$-$MoO_3$ and "alpha"-$MoO_3$.

DETAILED DESCRIPTION OF THE INVENTION

It has been found that aqueous molybdic acid and mixtures thereof with tungstic acid can be converted, in a spray-drying process, to novel amorphous powders of the formula, $H_2Mo_{1-x}W_xO_4$, wherein $0 \leq x < 1.0$. Thermal treatment of the amorphous powders affords a three-dimensional phase of the specified metal or mixed-metal oxides, designated "beta" or "$\beta$" herein. Differences in physical characteristics of "beta" and "alpha"-phase crystals make the two materials easily discernible. It has further been found that this "beta" phase of the specified metal and mixed metal oxides can be prepared in films by sputtering or spin coating. The compositions are useful as catalysts for the selective oxidation of methanol to formaldehyde. The specified compositions have further utility in the photochromism (yellow→blue→black) produced by conversion of the "beta"

phase to a hydrogen or lithium intercalate for electrochromic display devices.

Figure 5A:
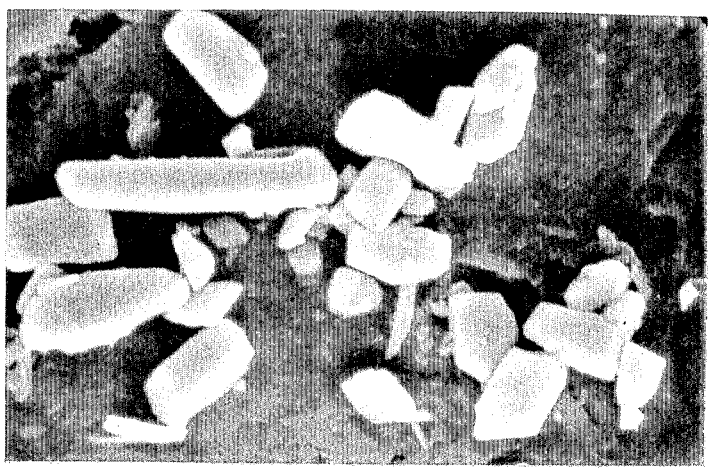
FIGS. 5a and 5b depict, respectively, scanning electron micrographs of "alpha"-$MoO_3$ and $\beta$-$MoO_3$.
Figure 5B:
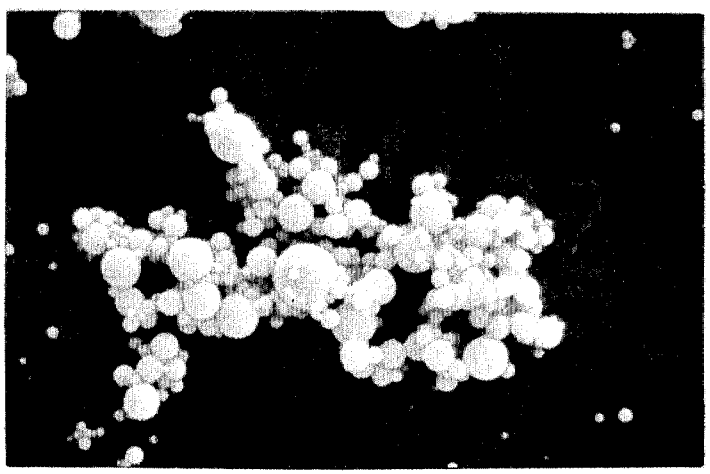

One advantage of the present methods is that they are capable of producing novel compositions of matter comprising $\beta$-Mo$_{1-x}$W$_x$O$_3$, wherein $0 \leq x < 0.5$, and preferably x is 0. This phase of the specified metal or mixed-metal oxide has a distorted three dimensional ReO$_3$ structure based on corner-linked octahedra as shown in FIG. 1. The structure is further characterized by the Raman spectrum shown in FIG. 3 and the powder x-ray data of Table 1., shown below. Microscopic examination (FIGS. 5a and 5b) shows that MoO$_3$ particles of the beta phase are spherical and particles of the alpha phase are in the form of platelets. Hydrogen or deuterium intercalates (bronzes) of the compositions can be prepared by treating the compositions with a reducing agent and hydrogen. Lithium bronzes can be prepared by treating the compositions with a (non-protonic) reducing agent and a lithium agent.

Figure 2:
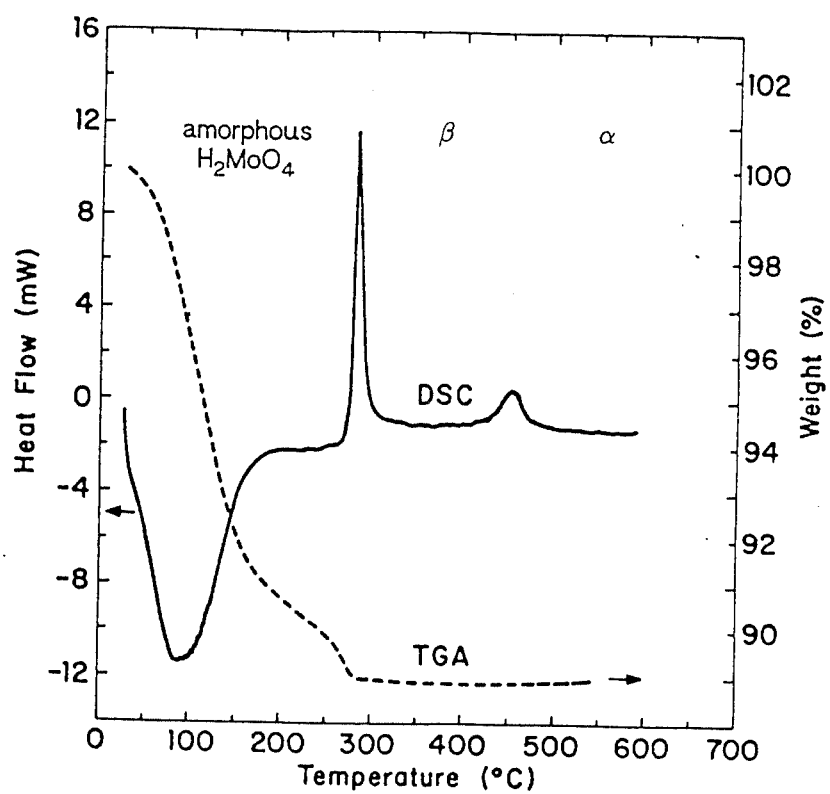
FIG. 2 shows TGA and DSC curves for amorphous $H_2MoO_4$.

It was known that boiling of a molybdic acid solution results in the precipitation of a layered phase of MoO$_3$ described herein as "alpha"-MoO$_3$. It has been found that spray drying aqueous molybdic acid and mixtures thereof with tungstic acid results in the formation of a novel amorphous powder of formula H$_2$Mo$_{1-x}$W$_x$O$_4$, wherein $0 \leq x < 1.0$. The thermogravimetric analysis (TGA) curve for amorphous molybdic acid is shown in FIG. 2. A comparison of the TGA curve of this spray-dried form of H$_2$MoO$_4$ with the TGA curves for the two known crystalline polymorphs of H$_2$MoO$_4$, yellow and white, shows that these materials are not isostructural. Reference to this spray-dried material as a molybdic acid, H$_2$MoO$_4$, as opposed to a molybdenum trioxide hydrate, MoO$_3$.H$_2$O, is based not only on the obvious differences in crystallinity and thermal decomposition profile, but also on differences in water solubility and pH of the resulting solution. The true hydrates are only sparingly soluble in water with a pH for saturated solutions of roughly 3.5, whereas the spray-dried H$_2$MoO$_4$ has a high solubility (>1M) and produces a solution having a pH of about 1.5.

The differential scanning calorimetry (DSC) curve of FIG. 2 describes the structural chemistry of amorphous H$_2$MoO$_4$. The figure shows that this spray-dried material loses water endothermically between ambient temperature and roughly 250° C. At 250° C., with substantial dehydration, the spray-dried powder is still amorphous to x-rays. Upon further heating, the DSC curve of this material exhibits a sharp exotherm at about 280° C. associated with complete water removal and a change from an amorphous to a crystalline state. The resulting yellow crystalline material is $\beta$-MoO$_3$ herein. Continued heating results in the transformation, at about 450° C., of $\beta$-MoO$_3$ to the layered phase of MoO$_3$, designated "alpha"-MoO$_3$ herein. Since the phase change "beta"→"alpha" is exothermic, $\beta$-MoO$_3$ is not the thermodynamically stable phase. However, the moderately high transformation temperature implies that $\beta$-MoO$_3$ is kinetically stable at or near ambient temperature. It has been found that the stability of the "beta"-phase can be improved by tungsten substitution, as evidenced by the increased "beta"→"alpha" tranformation temperature of about 530° C. for Mo$_{0.95}$W$_{0.05}$O$_3$.

Although the microstructure (morphology) of the powder does not appear to change as the amorphous molybdic acid converts to crystalline "beta"-MoO$_3$, the color of the material changes from pale green to yellow. The yellow color signals the formation of an ReO$_3$-like phase of MoO$_3$, analogous to WO$_3$. Since the low temperature synthesis method of this invention precludes single crystal growth, the structure type of "beta"-MoO$_3$ was determined by powder x-ray diffraction, and confirmed by Raman spectroscopy and by intercalation chemistry.

The general structural features of the beta phase were revealed by powder x-ray diffraction. The x-ray powder pattern of $\beta$-MoO$_3$ indexed to a monoclinic unit cell while the systematic absences indicated the space group P2$_1$/c. The similarity between the lattice parameters of "beta"-MoO$_3$ and the "theta"- and "eta"- phases of W$_{0.4}$Mo$_{0.6}$O$_3$ shown in Table 1 suggests a close structural relationship.

TABLE 1

| Composition | temp. (°C.) | Powder x-ray data for $\beta$-MoO$_3$. | | | | | |
| --- | --- | --- | --- | --- | --- | --- | --- |
| | | a ($10^{-1}$ nm) | b ($10^{-1}$ nm) | c ($10^{-1}$ nm) | "beta" (o) | Vol. [($10^{-1}$ nm)$^3$] | density (g/mL) |
| "beta"-MoO$_3$ | about 25 | 7.122 | 5.374 | 5.565 | 91.88 | 212.9 | 4.49 |
| "beta"-Mo$_{0.95}$W$_{0.05}$O$_3$ | about 25 | 7.130 | 5.358 | 5.559 | 91.94 | 212.3 | 4.50 |
| "eta"-W$_{0.4}$Mo$_{0.6}$O$_3$ (a) | 250 | 7.189 | 5.372 | 5.551 | 91.36 | 214.3 | 5.55 |
| "theta"-W$_{0.4}$Mo$_{0.6}$O$_3$ (a) | 550 | 7.206 | 5.409 | 5.574 | 90.00 | 217.3 | 5.47 |
| "alpha"-MoO$_3$ (b) | about 25 | 3.962 | 13.858 | 3.697 | 90.00 | 203.0 | 4.71 |

(a) Salje, E., Gehlig, R., Viswanathan, K., J. Solid State Chem., 25:239 (1978).
(b) Kihlborg, L., Arkiv Kemi, 21:357 (1963), and references therein.

The structure of "theta"-W$_{0.4}$Mo$_{0.6}$O$_3$ had been solved and shown to be related to an antiferroelectric distortion of the ReO$_3$ structure. The atomic coordinates of the "theta"-phase were transformed from Cmc2$_1$ to P2$_1$/c and used to generate a calculated powder pattern for $\beta$-MoO$_3$. A reasonable agreement between the observed and calculated for $\beta$-MoO$_3$ implies that the $\beta$-MoO$_3$ structure is indeed based on a distortion of the cubic ReO$_3$ (corner-linked octahedra) structure.

Figure 3:
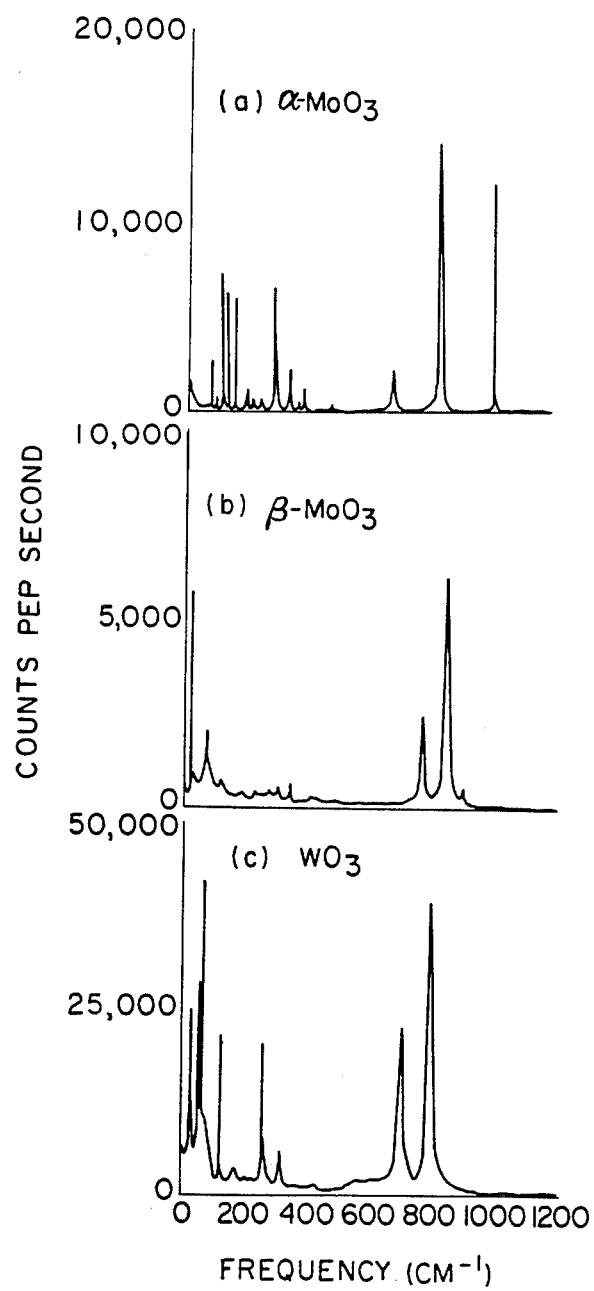
FIG. 3 shows Raman spectra for "alpha"-$MoO_3$, $\beta$-$MoO_3$, and $WO_3$.
Figure 4:
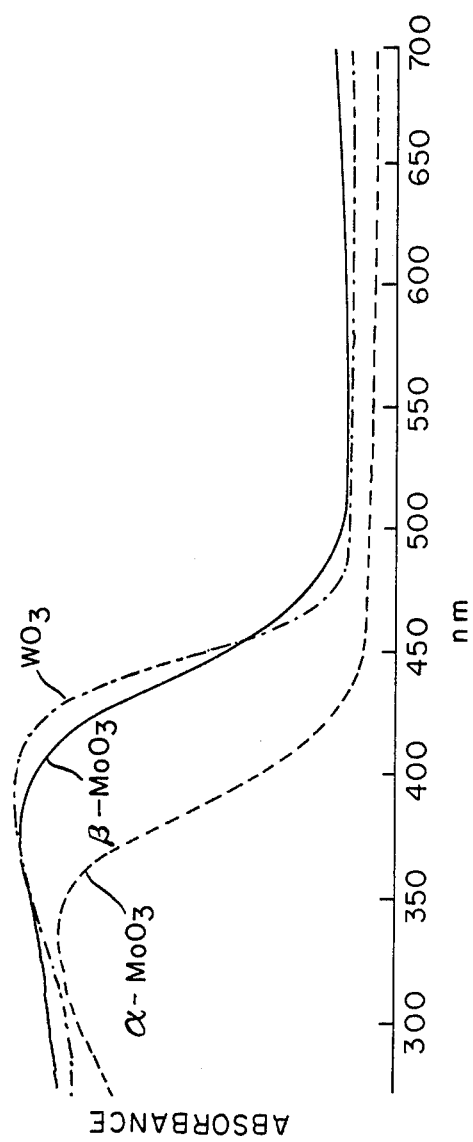
FIG. 4 shows electronic absorption spectra for "alpha"-$MoO_3$, $\beta$-$MoO_3$, and $WO_3$.

The Raman spectrum of $\beta$-MoO$_3$ also suggests a close structural similarity of the present composition and WO$_3$. FIG. 3 compares the Raman spectra of alpha-MoO$_3$, $\beta$-MoO$_3$, and WO$_3$. A comparison of the alpha- and beta-phases of MoO$_3$ in the Mo-O stretching region (above 600 cm$^{-1}$) clearly indicates that the structures are dissimilar. Most noticeably, the peak associated with the unique molybdenyl bond (Mo=O: 1000 cm$^{-1}$), which is responsible for the layered structure of alpha-MoO$_3$, is absent from the $\beta$-MoO$_3$ spectrum. Moreover, although the site symmetry of the molybdenum atoms of beta-MoO$_3$ is not known in detail, a comparison of the $\beta$-MoO$_3$ and WO$_3$ spectra reveals a correspondence between peaks in the metal-oxygen stretching region for the two trioxides, with the tungsten oxide peaks shifted towards lower frequencies. The extra peak observed in the $\beta$-MoO$_3$ spectrum (900 cm$^{-1}$) most likely indicates that the site symmetries, while similar, are not identical. One consequence of the structure is that the density of $\beta$-MoO$_3$ is lower than that of the layered "alpha"-MoO$_3$ (Table 1).

In the present invention, compositions of matter comprising $\beta$-Mo$_{1-x}$W$_x$O$_3$, wherein $0 \leq x < 1.0$, are prepared by the method comprising spray-drying solutions of molybdic acid or molybdic and tungstic acids in appropriate concentrations and heating the resulting powder at a temperature of from about 275° C. to about 450° C., and preferably from about 325° C. to about 375° C. The invention further provides a method for preparing films of the specified compositions comprising sputtering a molybdenum or mixed metal oxide target in appropriate concentrations. Depending on the sputtering conditions, films can be made to crystallize as either alpha-phase or the beta-phase of this invention. It has been found that the beta-phase is obtained when a suitable target is sputtered onto a thermally floating substrate in an atmosphere comprising oxygen and an inert gas, wherein the oxygen is in an amount from about 5 to about 50 volume percent. As used herein, the expression "thermally floating substrate" means that the surface temperature of the substrate is controlled primarily by the sputtering activity. In practice, the surface temperature of the substrate during sputtering is from about 150° C. to about 275° C. A partial list of suitable substrates includes glass, paper, metals, various oxides, polymeric materials and others. Preferably, the sputtering is conducted in an atmosphere comprising argon and oxygen. An alternative method for preparing films of the specified compositions comprises spin coating a solution containing the present compositions.

The methods of the invention are capable of producing novel compositions of matter comprising $\beta$Mo$_{1-x}$W$_x$O$_3$, wherein $0 \leq x < 0.05$. Hydrogen or deuterium intercalates (bronzes) of these novel compositions can be prepared by treating the compositions with a reducing agent and a source of hydrogen. Powder x-ray data for H$_{1.23}$MoO$_3$ are shown in Table 2.

TABLE 2

| Powder X-Ray Data for H$_{1.23}$MoO$_3$ | | | | | |
|---|---|---|---|---|---|
| I | 2θ° | h | k | l | d(obs) (10$^{-1}$ nm) | d(cala) (10$^{-1}$ nm) |
| 100 | 23.469 | 2 | 0 | 0 | 3.787 | 3.7871 |
| 45 | 33.417 | 2 | 2 | 0 | 2.679 | 2.6779 |
| 4 | 37.469 | 3 | 1 | 0 | 2.396 | 2.3952 |
| 9 | 41.256 | 2 | 2 | 2 | 2.186 | 2.1865 |
| 1 | 44.707 | 3 | 2 | 1 | 2.025 | 2.0243 |
| 18 | 48.026 | 4 | 0 | 0 | 1.893 | 1.8936 |
| 30 | 54.080 | 4 | 2 | 0 | 1.694 | 1.6937 |
| 15 | 59.778 | 4 | 2 | 2 | 1.547 | 1.5461 |
| 7 | 70.246 | 4 | 4 | 0 | 1.339 | 1.3390 |
| 10 | 75.197 | 6 | 0 | 0 | 1.262 | 1.2624 |

Lithium bronzes can be prepared by treating these novel compositions with a (non-protonic) reducing agent and a lithium agent. The intercalation of $\beta$-MoO$_3$ by hydrogen confirms the ReO$_3$-like structure of this metastable $\beta$-MoO$_3$ phase. The lattice parameters of these related hydrogen bronzes are listed in Table 3.

TABLE 3

| Cubic lattice constants for hydrogen bronzes. | |
|---|---|
| Composition | × 10$^{-1}$ nm |
| H$_{0.5}$MoO$_3$ | 7.574 |
| H$_{0.5}$WO$_3$ (a) | 7.556 |
| H$_{0.98}$Mo$_{0.7}$W$_{0.31}$O$_3$ (b) | 7.580 |

(a) Wiseman, P. J., Dickens, P. G., J. Solid State Chem., 6:374 (1973).
(b) Hibble, S. J., Dickens, P. G., Mat. Res. Bull., 20:343 (1985); and references discussed therein.

Contacting a composition of the present invention with a reducing agent and a source of hydrogen results in the formation of a hydrogen bronze. Examples include zinc/hydrochloric acid and Na$_2$S$_2$O$_4$/H$_2$O. Another example is hydrogen spillover, in which hydrogen (H$_2$) acts as both reducing agent and the source of the intercalated hydrogen. The reactions are conducted under generally mild conditions, such as the procedure presented in Example 5 for H$_{1.23}$MoO$_3$.

Lithium bronzes can be produced via the reaction of $\beta$-MoO$_3$ with a non-protonic reducing agent and a lithium agent, for example, an alkyl lithium, lithium aluminum hydride or lithium borohydride. Preferably, the compositional limits for the bronzes of hydrogen, deuterium, and lithium are H$_x$MoO$_3$ ($0 < x \leq 1.25$), D$_x$MoO$_3$ ($0 < x \leq 1.25$) and Li$_x$MoO$_3$ ($0 < x \leq 2$).

The present invention also provides a method for selective oxidation of methanol to formaldehyde employing $\beta$-Mo$_{1-x}$W$_x$O$_3$, wherein $0 \leq x < 1.0$, as catalysts. The reaction can be carried out using techniques known in the art in a variety of suitable reactors. The method comprises contacting methanol and oxygen in the presence of a catalytically effective amount of a composition of matter comprising $\beta$-Mo$_{1-x}$W$_x$O$_3$, wherein $0 \leq x < 1.0$, and preferably wherein $0 \leq x \leq 0.5$ and most preferably wherein x is 0. Air provides a suitable source of molecular oxygen. Preferably, the selective oxidation of methanol to formaldehyde is conducted at a temperature of from about 200° to about 450° C., and most preferably from about 250° to about 400° C. Preferred operating pressures are from about 1 to about 100 kPa, and most preferably from about 6 to about 15 kPa.

The methods and compositions of the present invention are further defined by the following examples wherein all parts and percentages are by weight and degrees are Celsius, unless otherwise stated.

EXAMPLE 1

Preparation of $\beta$-MoO$_3$

An aqueous solution prepared from 25 g of Na$_2$MoO$_4$.2H$_2$O and 100 mL of H$_2$O (about 1M with pH of about 9) was passed through a cation exchange column loaded with 500 g of a resin commercially available from Fischer Scientific under the registered trademark Rexyn 101 (H). The pH and the sodium content of the effluent solution were monitored. The pH of the resulting molybdic acid solution was determined to be about 1.7 and the sodium content less than 10-3 ppm. The solution was then spray-dried with a Buchi 190 Mini Spray Dryer (inlet/outlet temperatures of 180° and 80°, respectively). The resulting powder was observed to have a pale greenish tint.

The composition of the powder was determined by thermogravimetric analysis to be H$_2$MoO$_4$ (H$_2$O weight loss=11.12%). Additionally, the spray-dried powder was found to dissolve in water exothermically and to be amorphous to x-rays. This amorphous molybdic acid powder was heated at 300° for 1 hour in oxygen to produce crystalline β-MoO₃. The freshly prepared β-MoO₃ was observed to have a yellow coloration similar to WO₃. The β-MoO₃ was also determined to be substanially different from "alpha"-MoO₃ by a comparison of their powder x-ray diffraction patterns and Raman spectra. Elemental analysis was performed by Galbraith Laboratories (Knoxville, Tenn.). Because the method of preparation involved proton exchange for sodium ions, samples were analyzed routinely for sodium. The results for the β-MoO₃ were: Mo-66.6(2)% (66.65% calc.); Na-0.025(15)%.

EXAMPLE 2

Preparation of $\beta\text{-Mo}_{0.95}W_{0.05}O_3$ $\beta\text{-Mo}_{0.95}W_{0.05}O_3$ was prepared according to a method similar to that described for β-MoO₃ in Example 1. Equimolar (1M) solutions of molybdic and tungstic acid were made by proton exchange from the appropriate sodium metallate solutions and mixed in a 19(Mo)/1(W) volume ratio. The resulting solution was spray dried to form an amorphous powder. The spray-dried powder was heated at 300° for 1 hour in oxygen to give $Mo_{0.95}W_{0.05}O_3$, which, based on a comparison of powder patterns, appeared isostructural with β-MoO₃. Analysis of the $Mo_{0.95}W_{0.05}O_3$ was as follows: Mo-61.3(2)% (61.44% calc.); W-6.3(2)% (6.20% calc.); Na-0.018(15)%.

EXAMPLE 3

Preparation of $\beta\text{-Mo}_{0.5}W_{0.5}O_3$

A 1(Mo)/1(W) mixture of equimolar (1M) acids spray-dried and heat treated according to a method similar to that outlined in Example 1 resulted in the formation of $\alpha\text{-Mo}_{0.5}W_{0.5}O_3$. Analysis of the $Mo_{0.5}W_{0.5}O_3$ was as follows: Mo-25.6(2)% (25.53% calc.); W-48.7(2)% (48.92% calc.); Na-0.022(15)%.

EXAMPLE 4

Preparation of $\beta\text{-Mo}_{0.95}W_{0.05}O_3$ $\beta\text{-Mo}_{0.95}W_{0.05}O_3$ was prepared by boiling a mixed acid solution of molybdic and tungstic acid [19(Mo)/1(W) volume ratio] to dryness. The x-ray diffraction pattern for this material was identical to that of the material described in Example 2. In constrast, boiling a pure molybdic acid solution resulted in the formation of the normal layered "alpha"-MoO₃ as determined by powder x-ray diffraction.

EXAMPLE 5

Preparation of Hydrogen Bronzes of β-MoO₃

Hydrogen bronzes of β-MoO₃ were formed by hydrogen spillover. Platinum-containing (<0.5% by weight) β-MoO₃ samples were prepared by drying 5 grams of the β-MoO₃ from Example 1 wetted with a chloroplatinic acid solution (about 0.06 grams in 10 mL). The dried platinum-containing β-MoO₃ samples then were contacted with hydrogen gas at ambient pressure and 100° for three hours. The resulting material was subsequently handled in a nitrogen atmosphere to avoid oxidation. The resultant bronzes appeared a dark blue-violet and analyzed as $H_{1.23}MoO_3$. Analysis for $H_{1.23}MoO_3$:H-0.85(3)%; Mo-66.0(2)%; Pt-0.4(1); Na-0.020(15)%.

EXAMPLE 6

Preparation of Hydrogen Bronzes of β-MoO₃

Hydrogen bronzes of β-MoO₃ were formed according to a method similar to that described in Example 5 except that the reaction temperature was ambient temperature and the reaction time was 1 hour. The resulting dark blue bronze analyzed as $H_{0.56}MoO_3$.

EXAMPLE 7

Preparation of Hydrogen Bronzes of β-MoO₃

Hydrogen bronzes of β-MoO₃ were formed by reaction with sodium dithionite. 5 g of β-MoO₃ was suspended in 100 mL of H₂O and cooled to 0° in an ice bath. To this suspension, 0.5 grams of sodium dithionite was added and the resulting suspension was stirred for 3 hours. An additional 1.5 g of Na₂S₂O₄ were then added to the suspension while still at 0° in the ice bath and the resulting mixture was allowed to stir for another 3 hour period. Subsequently, 3 more grams of Na₂S₂O₄ were added to the mixture at 0° in the ice bath and the resulting mixture was allowed to stir for 24 hours during which period the mixture warmed to ambient temperature. The resulting material was washed with deoxygenated water in a nitrogen-filled glove bag and allowed to dry under the nitrogen atmosphere. The resulting blue-black bronze was isomorphous (as determined by x-ray diffraction) with the bronze prepared in Example 5 and analyzed as $H_{1.25}MoO_3$: H-0.87(3)%; Mo-66.1(2)%; Na-0.022(15)%.

EXAMPLE 8

Preparation of Hydrogen Bronzes of β-MoO₃

Hydrogen bronzes of β-MoO₃ were formed according to a method similar to that described in Example 7 except that 0.25 g of Na₂S₂O₄ was added at 0° in the ice bath and stirred for three hours; a second 0.25 g of Na₂S₂O₄ was added at 0° in the ice bath and stirred for three hours; and a final 0.50 g of Na₂S₂O₄ was added at 0° in the ice bath and stirred for 24 hours during which period the reaction mixture warmed to ambient temperature. The resulting washed and dried dark blue material was analyzed as $H_{0.33}MoO_3$.

EXAMPLES 9–12

Preparation of Hydrogen Bronzes of β-MoO₃

Deuterium bronzes of β-MoO₃ were formed according to methods similar to those described in Examples 5–8 except that deuterium was substituted for hydrogen and deuterated water was substituted for normal water.

EXAMPLE 13

Preparation of Lithium Bronzes of β-MoO₃

Lithium bronzes were prepared by contacting lithium iodide and β-MoO₃ in acetonitrile. 2.0 g of lithium iodide were dissolved in 50 mL of acetonitrile. To this solution, 2.0 g of β-MoO₃ were added at ambient temperature and the resulting mixture was allowed to react for 1 week with stirring. The resulting material was filtered, washed with fresh acetonitrile and dried under nitrogen to avoid oxidation. The resulting lithium bronze was blue.

EXAMPLE 14

Preparation of Lithium Bronzes of β-MoO₃

Lithium bronzes were prepared by contacting n-butyllithium and β-MoO₃ in hexane. To 25 mL of a 1.6M solution of n-butyllithium in hexane were added 2 g of β-MoO₃ at 0° in an ice bath. The resulting reaction mixture was stirred for 24 hours during which time the reaction was allowed to warm to ambient temperature. The resulting material was then filtered, washed with fresh hexane, and dried under nitrogen to avoid oxidation. The resulting lithium bronze appeared blue-black.

EXAMPLE 15

Preparation of β-MoO₃ by Sputtering

Thin films of β-MoO₃ were prepared by RF sputtering from a 3" diameter MoO₃ target (or cathode), epoxied to a water-cooled stainless steel backing plate. The vacuum chamber was initially pumped to about $2 \times 10^{-6}$ Torr by a diffusion pump with a liquid nitrogen baffle. The substrates were $(2.54 \times 10^{-2}) \times (2.54 \times 10^{-2})$ m² glass coverslips placed on $(2.54 \times 10^{-2}) \times (7.62 \times 10^{-2})$ m² glass microscope slides, which rested on the anode table approximately $8 \times 10^{-2}$ m below the target. Sputtering was carried out with 1.2 Pa of Ar plus 0.13 Pa at a cathode potential of $-2000$ volts. The deposition rate, determined from measured film thicknesses of about 500 nm, was 5.65 nm/min. The deposited films were yellow in color. The thin films were characterized as β-MoO₃ by their x-ray diffraction patterns and Raman spectra as described in Example 1.

EXAMPLES 16-21 AND COMPARATIVE EXPERIMENT A

Selective Oxidation of Methanol to Formaldehyde

The compositions shown in Table 4 were evaluated as catalysts for selective oxidation of methanol to formaldehyde. Four grams of each composition were placed in a U-tube reactor made of ⅜" (0.95 cm) titanium tubing. To the reactor was fed air at 145 mL/min and methanol at 1.5 mL/hr. The methanol was vaporized before it entered the reactor. The pressure in the reactor was 6.9 kPa (1 atm) and the temperature was 250°. The effluent from the reactor was analysed by an online gas chromatograph. The results are shown in Table 4.

TABLE 4

Selective Oxidation of Methanol to Formaldehyde

| Ex. or Comp. Ex. | Catalyst | S.A. (m²/g) | Relative Reaction Rate per Surface Mo |
|---|---|---|---|
| 16 | β-Mo₀.₁W₀.₉O₃ | 2.9 | 0.4 |
| 17 | β-Mo¼W¾O₃ | 1.5 | 0.7 |
| 18 | β-Mo½W½O₃ | 0.8 | 0.6 |
| 19 | β-Mo¾W¼O₃ | 0.7 | 1.0 |
| 20 | β-Mo₀.₉₅W₀.₀₅O₃ | 2.6 | 1.7 |
| 21 | β-MoO₃ | 2.6 | 3.0 |
| A | α-MoO₃ | 2.7 | 0.1 |

We claim:

1. A method for preparing a composition of matter comprising β-Mo$_{1-x}$W$_x$O₃, wherein $0 \leq x < 1.0$, comprising spray-drying a solution of molybdic acid or molybdic and tungstic acids in appropriate concentrations and heating the resulting powder at a temperature of from about 275° C. to about 450° C.

2. A method as defined in claim 1, wherein the temperature is from about 325° C. to about 375° C.

3. A method as defined in claim 2, wherein x is 0.

4. A method for preparing a composition of matter comprising β-Mo$_{1-x}$W$_x$O₃, wherein $0 \leq x < 1.0$, comprising sputtering a molybdenum or mixed metal oxide target of molybdemum and tungsten in appropriate concentrations onto a thermally floating substrate in an atmosphere comprising oxygen and an inert gas, wherein the oxygen is in an amount from about 5 to about 50 volume percent.

5. A method as defined in claim 4, wherein the inert gas is argon.

6. A method as defined in claim 4, wherein x is 0.

7. A method for preparing a film of a composition of matter comprising β-Mo$_{1-x}$W$_x$O₃, wherein $0 \leq x < 1.0$, comprising spin coating a solution containing the composition.

8. A composition of matter comprising β-Mo$_{1-x}$W$_x$O₃, wherein $0 \leq x < 0.05$.

9. A composition of matter comprising a phase of Mo$_{1-x}$W$_x$O₃, wherein $0 \leq x < 0.05$, said phase having a distorted three dimensional ReO₃ structure based on corner-linked octahedra.

10. A composition of matter as defined in claim 9, wherein said phase has the Raman spectrum shown in FIG. 3.

11. A composition of matter as defined in claim 10, wherein said phase has the powder x-ray data of Table 1.

12. A composition of matter as defined in claim 11, wherein x is 0.

13. A composition of matter comprising a hydrogen or deuterium interchalate of the composition defined in claim 8.

14. A composition of matter comprising a lithium bronze of the composition defined in claim 8.

15. A composition of matter comprising amorphous H₂Mo$_{1-x}$W$_x$O₄, wherein $0 \leq x < 1.0$.

16. A composition of matter as defined in claim 15, wherein the amorphous H₂Mo$_{1-x}$W$_x$O₄ is H₂MoO₄ having the thermogravimetric analysis curve shown in FIG. 2.

17. A composition of matter as defined in claim 16, wherein the H₂MoO₄ has the differential scanning calorimetry curve shown in FIG. 2.

18. A method for preparing the composition of matter of claim 15 comprising spray-drying a solution of molybdic acid or molybdic and tungstic acids in appropriate concentrations.

* * * * *